(12) United States Patent
Rampi et al.

(10) Patent No.: US 8,226,581 B2
(45) Date of Patent: Jul. 24, 2012

(54) BITE FORCE GAUGE

(76) Inventors: Richard C. Rampi, Orlando, FL (US); Maria P. Rampi, Orlando, FL (US)

( * ) Notice: Subject to any disclaimer, the term of this patent is extended or adjusted under 35 U.S.C. 154(b) by 1002 days.

(21) Appl. No.: 12/180,026

(22) Filed: Jul. 25, 2008

(65) Prior Publication Data

US 2008/0281233 A1 Nov. 13, 2008

Related U.S. Application Data

(63) Continuation-in-part of application No. 11/638,165, filed on Dec. 13, 2006, now abandoned.

(51) Int. Cl.
*A61B 5/103* (2006.01)
*A61B 5/117* (2006.01)
*G01L 1/00* (2006.01)
*G01L 5/00* (2006.01)

(52) U.S. Cl. ............... 600/590; 600/587; 73/862.381

(58) Field of Classification Search .......... 600/590, 600/589, 587, 553, 557, 552, 550; 33/511–514; 73/862.581, 862.583, 862.584, 862.381, 73/862.454, 379.02–379.05, 78, 79, 81, 744; 433/68, 72
See application file for complete search history.

(56) References Cited

U.S. PATENT DOCUMENTS

| | | | | |
|---|---|---|---|---|
| 1,427,496 A | * | 8/1922 | Ono | 73/379.02 |
| 1,842,323 A | * | 1/1932 | Gluzek | 600/557 |
| 2,667,067 A | * | 1/1954 | Pocknee | 73/81 |
| 2,704,539 A | * | 3/1955 | Fisher | 600/557 |
| 3,611,807 A | * | 10/1971 | Brandell | 73/379.03 |
| 3,722,100 A | * | 3/1973 | Weisman et al. | 433/72 |
| 3,933,148 A | * | 1/1976 | Wyler et al. | 600/557 |
| 4,048,985 A | * | 9/1977 | Sasse | 600/591 |
| 4,530,496 A | * | 7/1985 | Smith et al. | 482/112 |
| 4,711,249 A | * | 12/1987 | Brooks | 600/561 |
| 4,791,940 A | * | 12/1988 | Hirschfeld et al. | 600/589 |
| 4,846,191 A | * | 7/1989 | Brockway et al. | 600/561 |
| 4,960,132 A | * | 10/1990 | Habekost | 600/589 |
| 4,979,898 A | * | 12/1990 | Rand | 433/72 |
| 5,460,522 A | * | 10/1995 | Scarffe | 433/72 |
| 5,897,510 A | * | 4/1999 | Keller et al. | 600/594 |
| 7,678,064 B2 | * | 3/2010 | Kuban | 600/557 |

FOREIGN PATENT DOCUMENTS

DE 4003947 * 8/1991

* cited by examiner

*Primary Examiner* — Max Hindenburg
*Assistant Examiner* — H. Q. Nguyen
(74) *Attorney, Agent, or Firm* — Dale J. Ream

(57) ABSTRACT

A bite force measuring device includes a handle having first and second ends. A measurement shaft extends outwardly from the handle first end and includes a distal end relative to the handle. A test plate is positioned on the measurement shaft. The measuring device includes a flexible reservoir positioned inside the measurement shaft that is in contact with the test plate that contains a generally incompressible fluid such that the flexible reservoir undergoes pressure changes when the test plate bears against the reservoir. A plunger shaft is operatively connected to the reservoir and is pushed outwardly therefrom when pressure in the reservoir is increased. The plunger shaft may include indicia indicative of a measurement of a relative bite force.

5 Claims, 6 Drawing Sheets

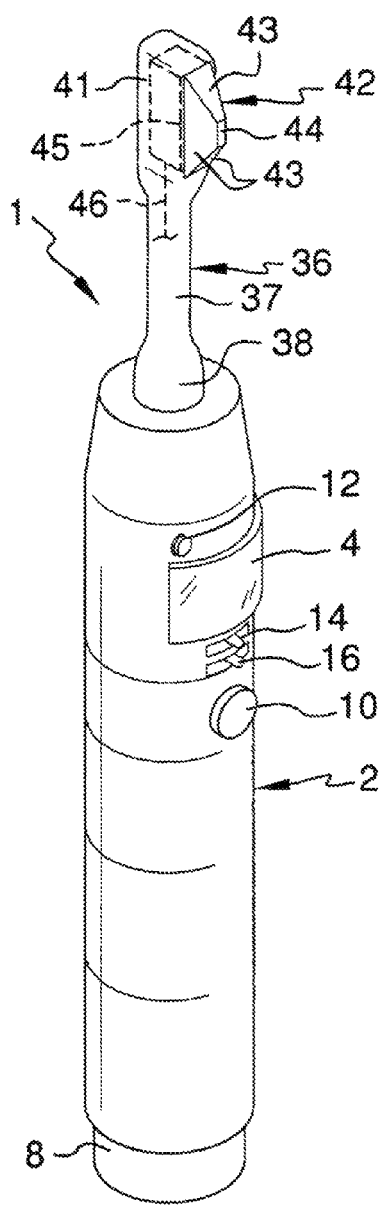
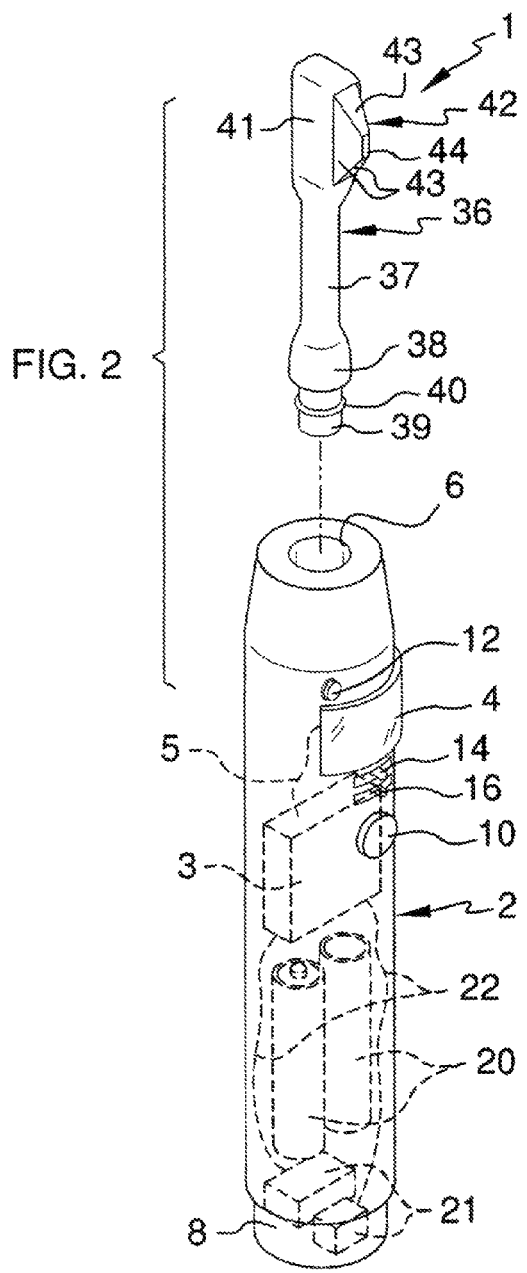
FIG. 1
FIG. 2

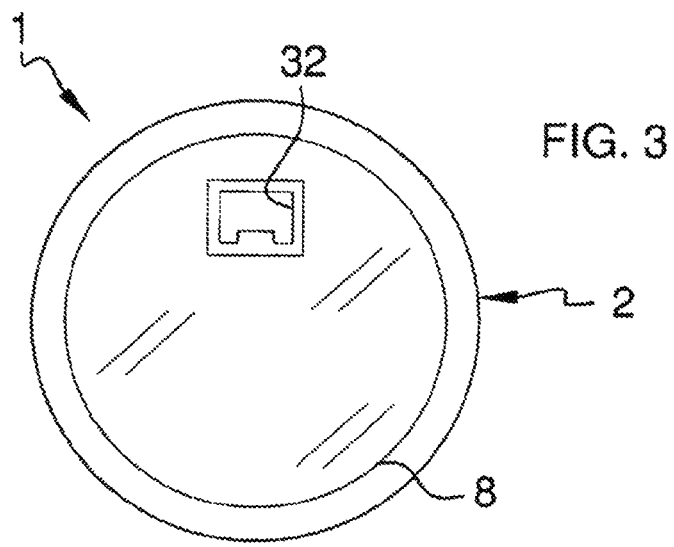
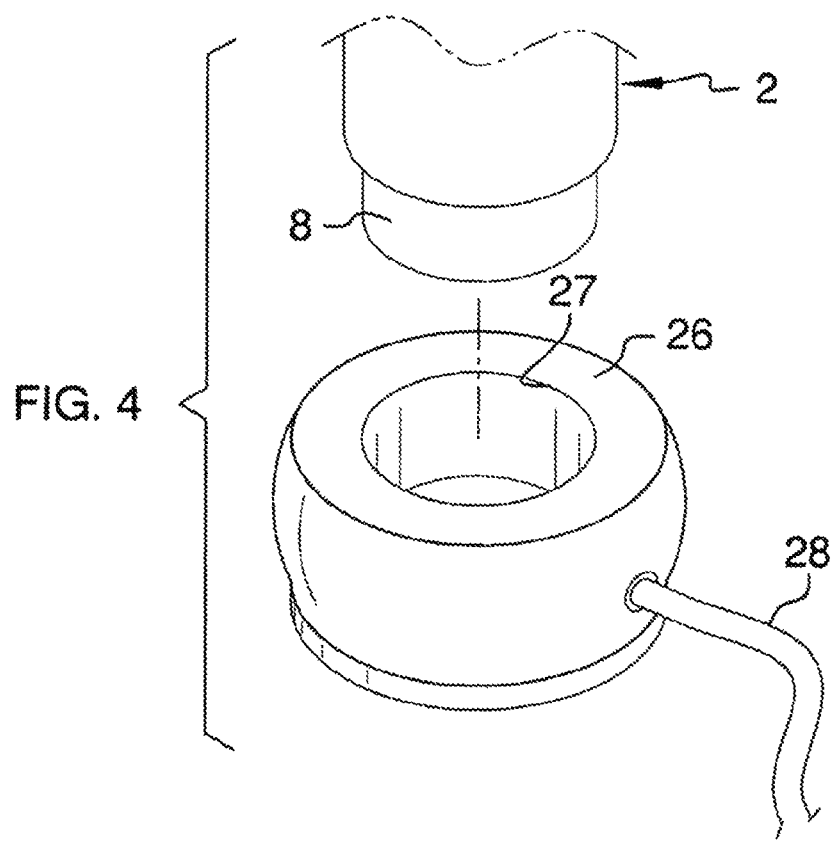

US 8,226,581 B2

BITE FORCE GAUGE

CROSS REFERENCE TO RELATED APPLICATION

The present application is a continuation-in-part of U.S. patent application Ser. No. 11/638,165, filed Dec. 13, 2006 now abandoned and titled "BITE FORCE GAUGE", which is incorporated herein by reference.

FIELD OF THE INVENTION

The present invention relates to dental appliances. More particularly, the present invention relates to a bite force measuring device which is adapted to measure the force of a bite in various dental diagnostic and treatment regimens.

BACKGROUND

In various dental diagnostic and treatment regimens, it is necessary to test the force or pressure of a patient's bite. A bite force measuring device is needed which is characterized by versatility, convenience, practicality and ease of use.

SUMMARY OF THE INVENTION

The present invention is generally directed to a bite measuring device. An illustrative embodiment of the bite force measuring device includes a handle, an attachment having a test plate carried by the handle, an electronic force transducer provided in the attachment in contact with the test plate, a central processing unit connected to the electronic force transducer, a display provided on the handle and connected to the central processing unit and a power source connected to the central processing unit.

In another embodiment of the present invention, a measuring device includes a handle having first and second ends. A measurement shaft extends outwardly from the handle first end and includes a distal end relative to the handle. A test plate is positioned on the measurement shaft. The measuring device includes a flexible reservoir positioned inside the measurement shaft that is in contact with the test plate that contains a generally incompressible fluid such that the flexible reservoir undergoes pressure changes when the test plate bears against the reservoir. A plunger shaft is operatively connected to the reservoir and is pushed outwardly therefrom when pressure in the reservoir is increased, allowing for a measurement of a relative bite force.

BRIEF DESCRIPTION OF THE DRAWINGS

The invention will now be described, by way of example, with reference to the accompanying drawings, in which:

FIG. 1 is a perspective view of an illustrative embodiment of the bite measuring device;

FIG. 2 is an exploded, perspective view of an illustrative embodiment of the bite measuring device, with an attachment element detached from a handle element of the bite measuring device;

FIG. 3 is a bottom view of an illustrative embodiment of the bite measuring device, more particularly illustrating a USB cable port provided in a bottom of the handle element of the bite measuring device;

FIG. 4 is an exploded, perspective view illustrating seating of a handle element (partially in section) of the bite measuring device in a battery charger;

DETAILED DESCRIPTION OF THE PREFERRED EMBODIMENT

Figure 5:
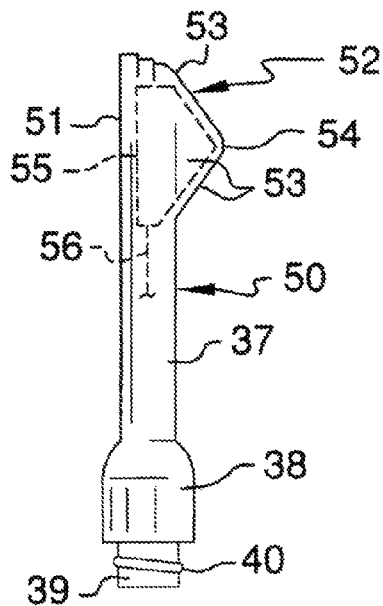
FIGS. 5-8 are side views of alternative attachments of the bite measuring device.

Referring to the drawings, an illustrative embodiment of the bite measuring device is generally indicated by reference numeral 1. The bite measuring device 1 includes an elongated handle 2. As shown in phantom in FIG. 2, a central processing unit (CPU) 3 is provided in the handle 2. A display 4, such as an LED (light emitting diode), for example, is provided on the handle 2. Wiring 5 connects the display 4 to the CPU 3.

As shown in FIG. 2, an insert opening 6, the purpose of which will be hereinafter described, is provided in a first end of the handle 2. A base 8 is provided on a second end of the handle 2. At least one battery 20 is provided in the handle 2. One pole of the at least one battery 20 is disposed in electrical contact with the CPU 3. At least one battery contact 21 is typically provided in the base 8, in electrical contact with the opposite pole of the at least one battery 20. Contact wiring 22 connects the at least one battery contact 21 to the CPU 3. As shown in FIG. 3, in some embodiments of the bite measuring device 1, a USB cable port 32 is provided in the base 8 and is connected to the CPU 3.

The at least one battery 20 may be rechargeable or disposable. As shown in FIG. 4, in the case of a rechargeable battery or batteries 20, the base 8 may be removable inserted in a charger opening 27 of an electric battery charger 26. A power cord 28 terminates in a plug (not shown) for insertion into a standard electrical outlet (not shown). Therefore, when the base 8 of the bite measuring device 1 is seated in the charger opening 27 of the battery charger 26, electrical power from the battery charger 26 recharges the battery or batteries 20.

An attachment 36 is adapted for detachable attachment to the handle 2. The attachment 36 typically includes an elongated attachment shaft 37 which terminates in an attachment base 38. As shown in FIG. 2, an insert 39 extends from the attachment base 38. A resilient, plastic or rubber seal ring 40 is typically provided on the insert 39. The insert 39 is adapted to be detachably inserted in the insert opening 6 of the handle 2 such that the seal ring 40 frictionally engages the interior surfaces of the insert opening 6. An attachment head 41, which is typically hard plastic, extends from the extending or distal end of the attachment shaft 37. A test plate 42, which is typically hard plastic, extends from the attachment head 41. The test plate 42 has a generally pyramid-shaped configuration and includes multiple side bite surfaces 43 and a terminal bite surface 44, which may have a generally concave shape.

As shown in phantom in FIG. 1, an electronic force transducer 45 is provided in the attachment head 41, in force-receiving contact with the test plate 42. A first electrical contact (not shown) is provided on the insert 39 and is connected to the electronic transducer 45 through transducer wiring 46. A second electrical contact (not shown) is provided in the insert opening 6 of the handle 2. Accordingly, when the insert 39 of the attachment 36 is inserted in the insert opening 6, the first electrical contact on the insert 39 engages the second electrical contact in the insert opening 6 to facilitate electrical contact between the CPU 3 and the attachment 36, for purposes which will be hereinafter described.

A power switch 10 is provided on the handle 2 and is connected between the CPU 3 and the batteries 20. A reset button 12 is for the purpose of calibrating in the absolute force mode. The accuracy of the device can be checked relative to a test spring with known force. If the device reading differs from this amount, the reseat button could be depressed and the device will be calibrated to this preset amount. When calibrating in the relative force mode, the patient is asked to apply to the maximum amount of comfortable force on a healthy neighboring control tooth. With maximum force applied, the operator depresses the reset button and the reading will be set and the test tooth is compared relative to the control tooth. The reset button 12 is provided on the handle 2 and connected to the CPU 3. A test mode switch 14 and a force mode selection switch 16, the purpose of which will be hereinafter described, are further provided on the handle 2 and connected to the CPU 3.

The electronic force transducer 45 is adapted to measure the bite force which is applied to the test plate 42. The CPU 3 is adapted to receive the bite force from the test plate 42. A memory is typically provided in the CPU 3 to facilitate storage of the bite force. The CPU 3 is configured to evaluate and measure the bite force according to one of two modes. According to the first mode, the CPU 3 evaluates the bite force in "absolute force", in which the CPU 3 indicates the magnitude of the bite force in either pounds or Newtons on the display 4. According to the second mode, the CPU 3 evaluates the bite force in "relative force", in which the CPU 3 compares the magnitude of the bite force of a test tooth measured by the electronic force transducer 45 with the bite force of a neighboring, healthy tooth. The relative force can be indicated on the display 4 on a scale of from 1 to 10, in which 1 indicates a weak tooth and 10 represents a strong tooth. The option between the "absolute force" mode and the "relative force" mode is selected using the test mode selection switch 14. In the "absolute force" mode, the option between pounds and Newtons is selected using the force mode selection switch 16.

In typical application, the bite measuring device 1 is used by a dental professional to diagnose any of various dental conditions such as to detect and/or evaluate a cracked tooth (not shown) in a patient's mouth (not shown). The bite measuring device 1 may also be used to quantify maximal occlusal load or biting force for patients with TMD or measuring progressive data to determine whether the biting force of a tooth is improving, deteriorating or remaining the same with time and degree of tooth injury, for example. Accordingly, the attachment 36 is attached to the handle 2. The bite measuring device 1 is turned on by depression of the force switch 10. After insertion of the attachment 36 in a patient's mouth (not shown), the test plate 42 is positioned between a test tooth on one jaw and a normal tooth on the opposite jaw. The patient applies bite force against the test plate 42 with the teeth. The bite force is measured by the electronic force transducer 45, which transmits the measured bite force to the controller 3. In turn, the controller 3 displays the measured bite force, either according to the "absolute force" mode or the "relative force" mode, as was described hereinabove, on the display 4. The dental professional can use the bite force to make a diagnosis and render treatment for the test tooth. Several trials of the bite force of the test tooth may be obtained.

The bite force is typically stored in the memory of the CPU 3. The stored bite force or forces can be uploaded to a computer (not shown) after connecting a USB cable (not shown) to the USB cable port 32 (FIG. 3) typically in the base 8 of the handle 2 and to a USB cable port (not shown) provided on the computer.

The bite measuring device 1 may be fitted with multiple interchangeable attachments of various designs and configurations depending on the type of tooth to be tested as well as the type of test which is to be carried out on the test tooth. For example, as shown in FIG. 5, an alternative attachment 50 which is suitable for implementation of the bite measuring device 1 includes an attachment head 51 which is typically hard plastic. A test plate 52, also typically hard plastic, is provided on the attachment head 51. The test plate 52 typically has a pyramidal shape and includes multiple side contact surfaces 53 and a terminal contact surface 54 which may have a generally concave shape. An electronic force transducer 55 is provided in the attachment head 51 and electrically connected to the CPU 3 through transducer wiring 56.

Figure 6:
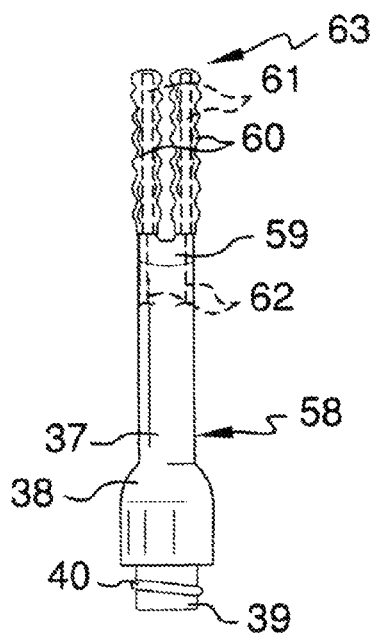

As shown in FIG. 6, another alternative attachment which is suitable for implementation of the bite measuring device 1 includes an attachment head 59. A test plate 63 includes a pair of spaced-apart fingers 60 which extend from the attachment head 59. The attachment head 59 and each of the fingers 60 may be soft rubber, for example. An electronic force transducer 61 (shown in phantom) is provided in each of the fingers 60 and is electrically connected to the CPU 3 through transducer wiring 62.

Figure 7:
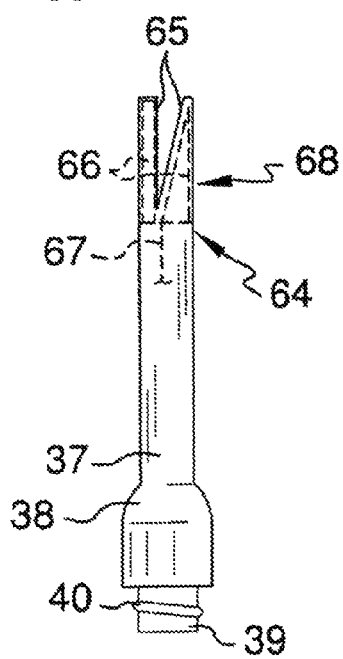

As shown in FIG. 7, still another alternative attachment 64 which is suitable for implementation of the bite measuring device 1 includes a test plate 68 having an adjacent tine 65 which extends from the attachment shaft 37. The test plate and tine are made of hard plastic. An electronic force transducer 66 extends into the tine 65 and is electrically connected to the CPU 3 through transducer wiring 67. In use, a roll of cotton (not shown) can be placed on the tine 65 and the bite force applied to the roll of cotton through the tine 65.

Figure 8:
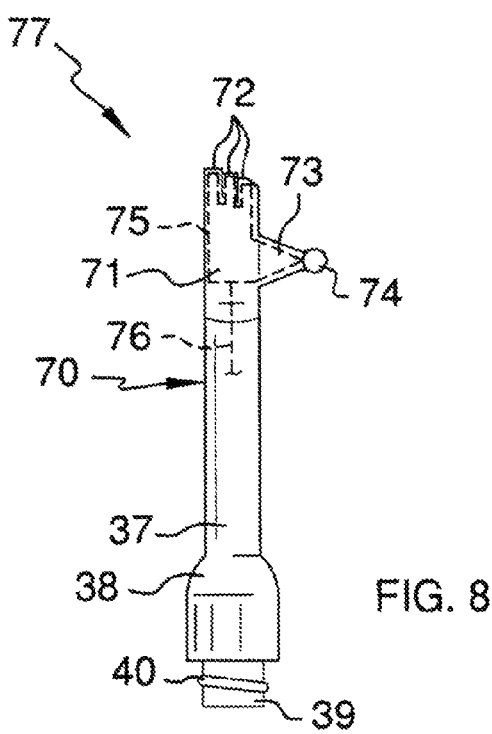

As shown in FIG. 8, yet another alternative attachment 70 which is suitable for implementation of the bite measuring device 1 includes an attachment head 71 which may be rubber or plastic. A test plate 77 is provided on the attachment head 71. A contact extension 73 extends from the attachment head 71, and a typically spherical contact head 74 terminates the extending or distal end of the contact extension 73. An electronic force transducer 75 is provided in the attachment head 71. The electronic force transducer 75 is electrically connected to the CPU 3 through transducer wiring 76.

A bite force measuring device 100 according to another embodiment of the present invention is shown in FIGS. 9a to 10e and includes a construction substantially similar to the construction described above except as specifically noted below. The bite force measuring device 1 first described was directed to an electrically or battery powered device for measuring bite force, whereas the bite force measuring device described below is directed to device using only mechanical structures and components to provide a unique and efficient device for measuring bite force.

Figure 9A:
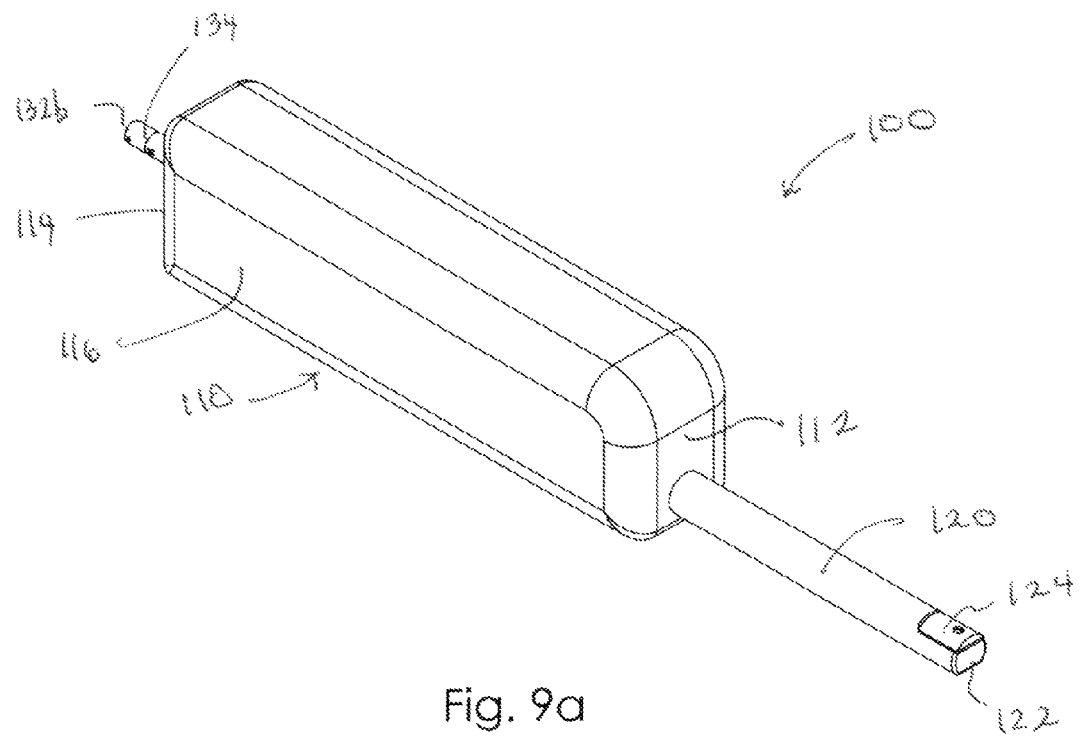
FIG. 9a is a perspective view of a bite force measuring device according to another embodiment of the present invention.
Figure 9B:
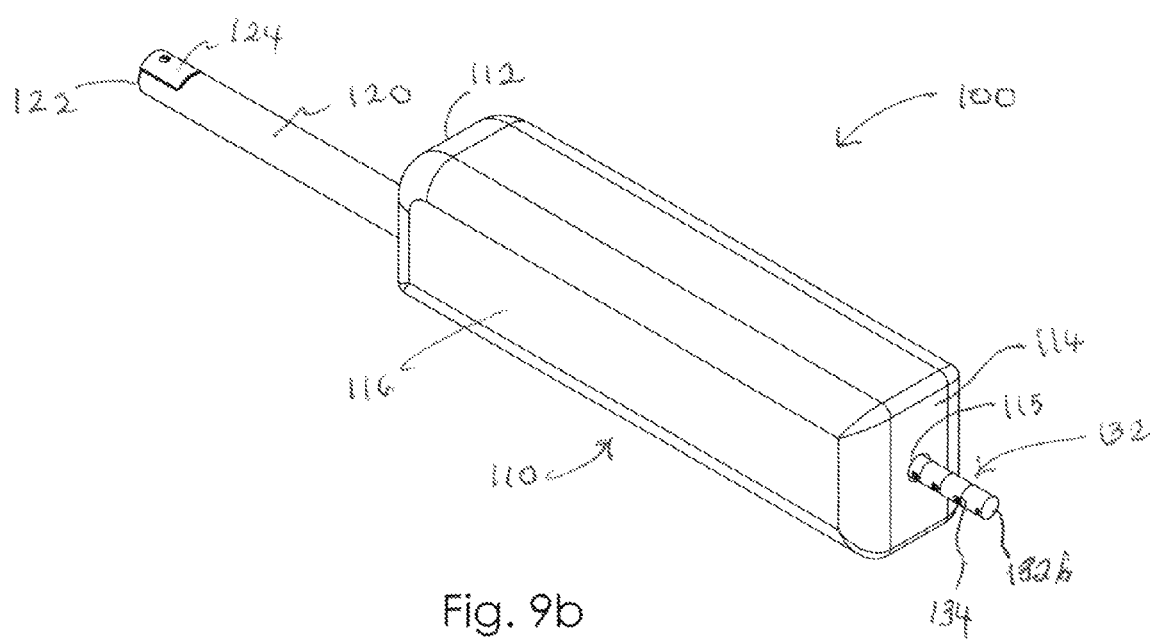
FIG. 9b is another perspective view of the measuring device as in FIG. 9a from another angle.

The measuring device 100 includes a handle 110 having first 112 and second 114 ends with one or more side walls 116 extending therebetween (FIGS. 9a and 9b). The handle 110 defines an interior space for containing other components as will be described below. An elongate measurement shaft 120 extends from the first end 112 of the handle 110 and includes a distal end 122 relative to the handle 110. The distal end 122 is intended to be inserted into a patient's mouth in use as will be described in greater detail later.

A test plate 124, preferably constructed of hard plastic, is positioned adjacent the terminal end of the measurement shaft 120 and configured for relative movement relative to the measurement shaft 120. A flexible reservoir 126 is positioned in the measurement shaft 120 adjacent to and in operative contact with the test plate 124 (FIG. 10d). The reservoir 126 is in fluid communication with an elongate channel 128 extending longitudinally through the measurement shaft 120 (FIG. 10b and 10c). The reservoir 126 may include a generally incompressible fluid, such as hydraulic fluid, the compression of which may generate high pressure changes that are easily measurable. The reservoir itself may be constructed of a high temperature stable material such as silicone rubber.

Figure 10A:
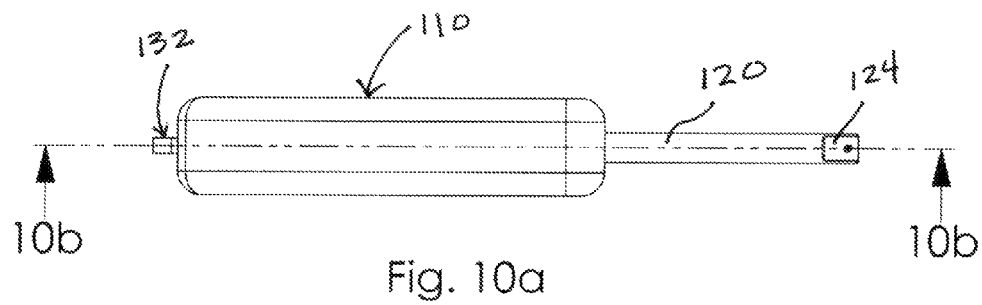
FIG. 10a is a top view of the measuring device as in FIG. 9.
Figure 10B:
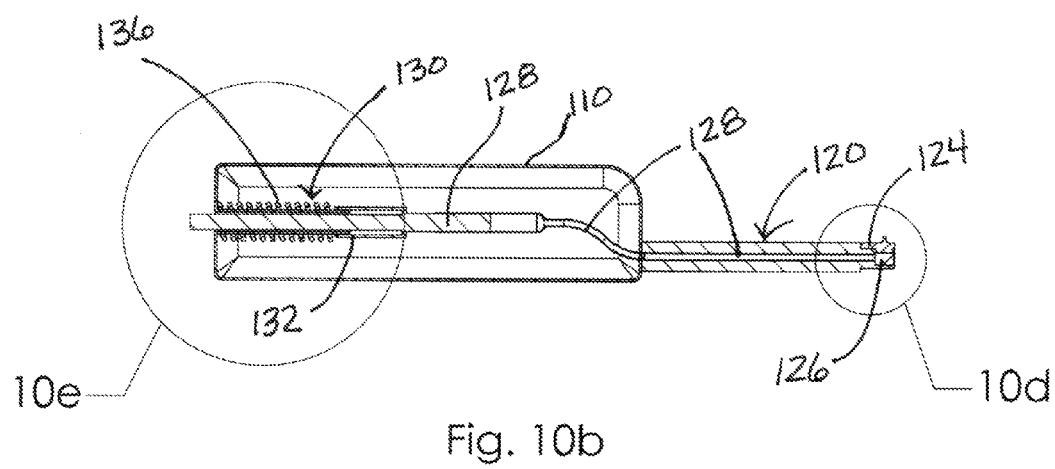
FIG. 10b is a sectional view taken along line 10b-10b of FIG. 10a showing a plunger shaft in an extended configuration.
Figure 10C:
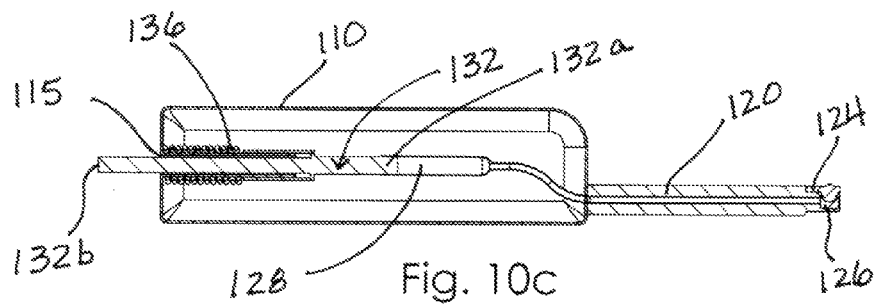
FIG. 10c is a sectional view as in FIG. 10b showing the plunger shaft in a retracted configuration.
Figure 10D:
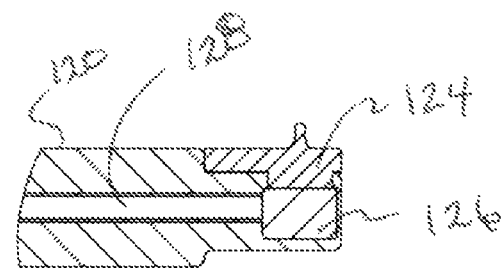
FIG. 10d is an isolated view on an enlarged scale taken from a portion of FIG. 10b.
Figure 10E:
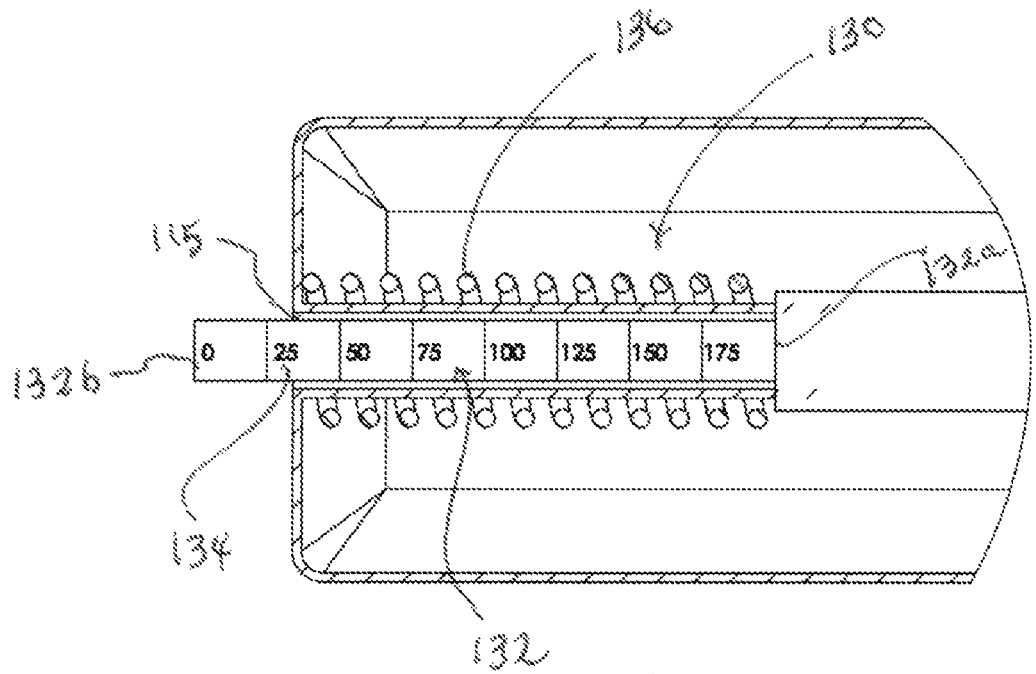
FIG. 10e is an isolated view on an enlarged scale taken from a portion of FIG. 10b.

A plunger assembly 130 is positioned within the interior space of the handle 110 and is in operative communication with the fluid reservoir 126 (FIGS. 10b, 10c, and 10e). The plunger assembly 130 includes a plunger shaft 132 having a first end 132a situated in the channel 128 and is configured for relative linear movement as pressure within the channel 128 changes. The second end 114 of the handle 110 defines an opening 115 through which the plunger shaft 132 (particularly the shaft second end) may extend. As pressure within the channel 128 increases, such as when a bite force is applied against the test plate 124, the plunger shaft 132 is linearly pushed outwardly from the reservoir 126 and channel 128 and extends outwardly from the handle 110 (FIG. 9b). The plunger shaft 132 may include indicia 134 imprinted thereon proximate a second/terminal end 132b thereof that is indicative of a quantity of pressure so that the degree of force imparted on the test plate 124 may be measured by the relative degree by which the plunger shaft 132 is extended from the handle 110.

The plunger assembly 130 further includes a compression spring 136 positioned adjacent the second end 114 of the handle 110 and operatively coupled to the plunger shaft 132. The spring 136 is compressed as the plunger shaft 132 is moved outwardly, the spring 136 biasing the shaft 132 to return inwardly when the force is removed. Therefore, the shaft 132 is biased by the spring 136 toward a retracted configuration.

In use, the bite force measuring device 100 may be manipulated by a user, e.g. a dentist, such that the test plate 124 at the terminal end of the measurement shaft 120 is positioned in a patient's mouth and, more particularly, such that the test plate 124 is adjacent a terminal surface of a tooth that is intended to be tested. Upon a user biting against the test plate 124, the flexible fluid reservoir 126 urges the plunger shaft 132 outwardly and the indicia 134 on the extent of the exposed terminal end of the shaft 132 may be read by a user.

Still other embodiments (not shown) are disclosed in which a bite force measurement may be indicated using a pressure gauge. More particularly, pressure applied to a test plate may be translated to a bent tube which, upon being bent slightly as a result, may turn a gear coupled to a pressure gauge. The translation of force from the test plate to the pressure gauge may still be accomplished using a fluid reservoir as described above or using another suitable means.

While the preferred embodiments of the invention have been described above, it will be recognized and understood that various modifications may be made in the invention and the appended claims are intended to cover all such modifications which may fall within the spirit and scope of the invention.

What is claimed is:

1. A patient bite force measuring device, comprising:
a handle having first and second ends and at least one side wall extending therebetween, said handle defining an interior space;
a measurement shaft fixedly attached to said handle first end and extending outwardly therefrom and having a distal end relative to said handle;
a test plate mounted adjacent said distal end of said measurement shaft;
a flexible reservoir positioned inside said measurement shaft in operative communication with said test plate and containing a generally incompressible fluid, said reservoir configured to experience a pressure change when said test plate bears against said reservoir;
wherein said incompressible fluid is hydraulic fluid;
an elongate channel in fluid communication with said reservoir and extending linearly in said interior space of said handle;
a plunger shaft having one end operatively positioned in said channel and configured for relative movement therein when a pressure of said fluid is increased or decreased;
wherein:
said handle second end defines an opening;
said plunger shaft includes a second end configured to extend through said opening, said plunger shaft moving outwardly through said opening when a relative pressure in said channel is increased and moving inwardly when a relative pressure in said channel is decreased;
a compression spring positioned adjacent said opening and being operatively connected to said plunger shaft, said spring being compressed when said plunger shaft is moved outwardly through said opening, said spring being normally biased to urge said plunger shaft inwardly relative to said handle; and
wherein:
said plunger shaft includes indicia proximate said plunger shaft second end that is indicative of a relative degree of pressure such that the patient bite force upon said test plate is visually measurable as said plunger shaft extends from said handle second end.

2. The measuring device as in claim 1, wherein said handle is constructed of a hard plastic material.

3. A patient bite force measuring device, comprising:
a handle having first and second ends and at least one side wall extending therebetween, said handle defining an interior space;
a measurement shaft extending outwardly from said handle first end and having a distal end relative to said handle;
a test plate mounted adjacent said distal end of said measurement shaft;
a flexible reservoir positioned inside said measurement shaft in operative communication with said test plate and containing a generally incompressible fluid, said reservoir configured to experience a pressure change when said test plate bears against said reservoir;
an elongate channel in fluid communication with said reservoir and extending linearly in said interior space of said handle;
a plunger shaft having a first end operatively positioned in said channel and configured for relative movement therein when a pressure of said fluid is increased or decreased;
said handle second end defines an opening;

said plunger shaft includes a second end configured to extend through said opening, said plunger shaft moving outwardly through said opening when a relative pressure in said channel is increased and moving inwardly when a relative pressure in said channel is decreased;

a compression spring positioned adjacent said opening and being operatively connected to said plunger shaft, said spring being compressed when said plunger shaft is moved outwardly through said opening; and wherein said plunger shaft includes indicia proximate said plunger shaft second end that is indicative of a relative degree of pressure such that the patient bite force upon said test plate is visually measurable as said plunger shaft extends from said handle second end.

4. The measuring device as in claim 3, wherein said spring is normally biased to urge said plunger shaft inwardly relative to said handle.

5. The measuring device as in claim 3, wherein said test plate is constructed of hard plastic.

* * * * *

UNITED STATES PATENT AND TRADEMARK OFFICE
CERTIFICATE OF CORRECTION

| | | |
|---|---|---|
| PATENT NO. | : 8,226,581 B2 | Page 1 of 4 |
| APPLICATION NO. | : 12/180026 | |
| DATED | : July 24, 2012 | |
| INVENTOR(S) | : Richard C. Rampi and Maria P. Rampi | |

It is certified that error appears in the above-identified patent and that said Letters Patent is hereby corrected as shown below:

On the title page, replace the informal drawing with the formal drawing of Fig 10b.

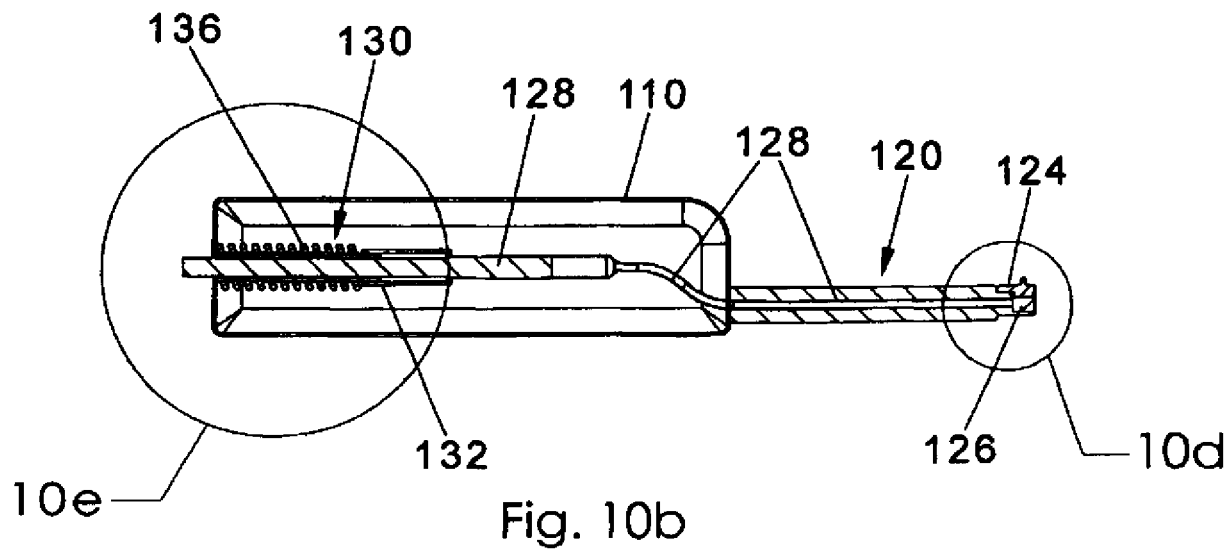

Fig. 10b

Signed and Sealed this
Second Day of October, 2012

David J. Kappos
*Director of the United States Patent and Trademark Office*

CERTIFICATE OF CORRECTION (continued)
U.S. Pat. No. 8,226,581 B2

On drawing Sheet 4 of 6, replace the informal drawing of Fig 9a and Fig 9b with the formal drawing of Fig 9a and Fig 9b.

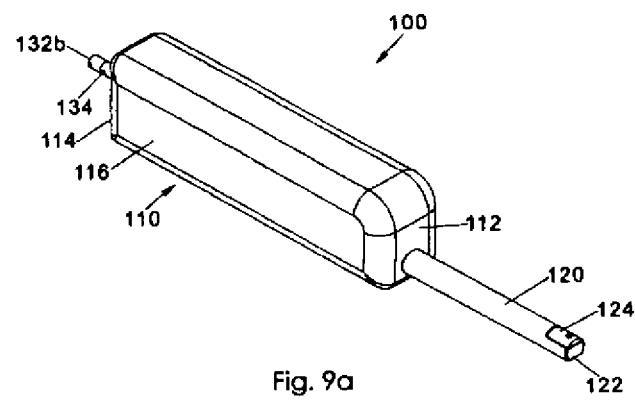

Fig. 9a

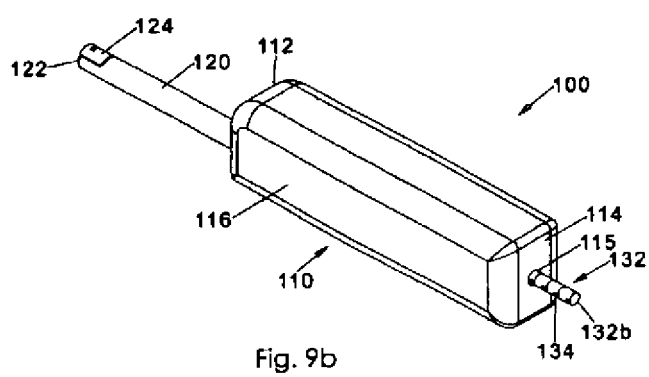

Fig. 9b

On drawing Sheet 5 of 6, replace the informal drawing of Fig 10a, Fig 10b and Fig 10c with the formal drawing of Fig 10a, Fig 10b and Fig 10c.
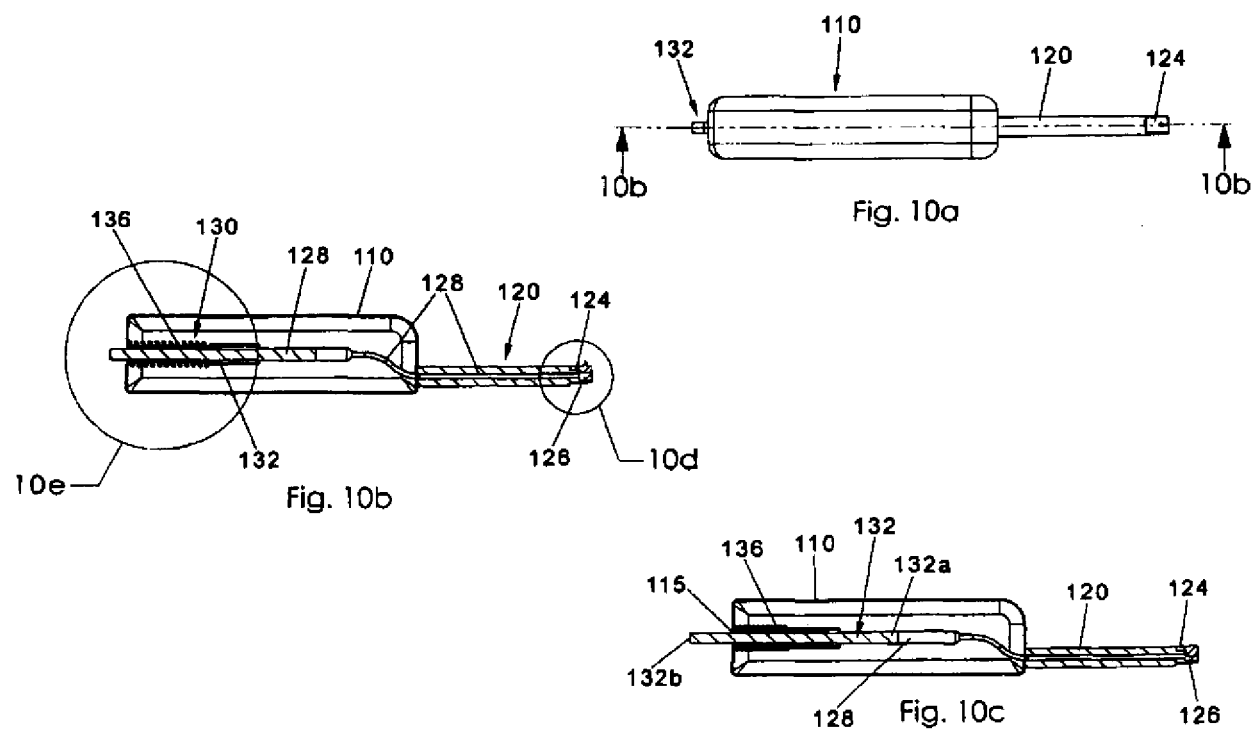

CERTIFICATE OF CORRECTION (continued)
U.S. Pat. No. 8,226,581 B2

On drawing Sheet 6 of 6, replace the informal drawing of Fig 10d and Fig 10e with the formal drawing of Fig 10d and Fig 10e.

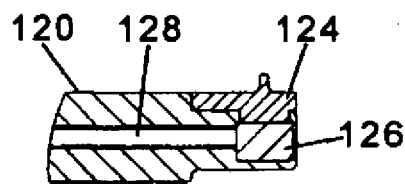

Fig. 10d

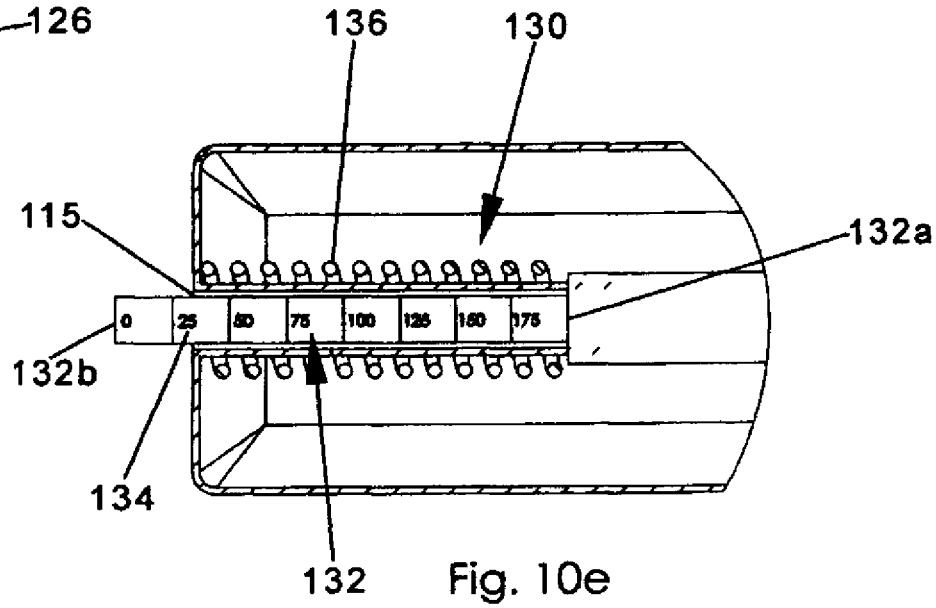

Fig. 10e